United States Patent [19]
Kuentz et al.

[11] Patent Number: 5,711,940
[45] Date of Patent: Jan. 27, 1998

[54] STABLE MICRODISPERSIONS AND MICROGELS BASED ON ACRYLIC POLYMERS, METHOD FOR OBTAINING THEM AND COMPOSITIONS, PARTICULARLY COSMETIC COMPOSITIONS, CONTAINING THEM

[75] Inventors: Annie Kuentz; Henri-Gérard Riess, both of Mulhouse; Alain Meybeck, Courbevoie; Jean-François Tranchant, Boigny sur Bionne, all of France

[73] Assignee: LVMH Recherche, France

[21] Appl. No.: 619,751

[22] PCT Filed: Sep. 30, 1994

[86] PCT No.: PCT/FR94/01145

§ 371 Date: Jun. 12, 1996

§ 102(e) Date: Jun. 12, 1996

[87] PCT Pub. No.: WO95/09874

PCT Pub. Date: Apr. 13, 1995

[30] Foreign Application Priority Data

Oct. 1, 1993 [FR] France .................. 93 11705

[51] Int. Cl.$^6$ .................. A61K 9/10; C08L 53/00; C08L 33/06
[52] U.S. Cl. .................. 424/61; 424/487; 424/501; 528/402; 525/94; 525/221; 525/227; 525/301; 525/302
[58] Field of Search .................. 424/61, 487, 501; 528/402; 525/94, 221, 227, 301, 302; 252/315.4

[56] References Cited

U.S. PATENT DOCUMENTS 4,558,075 12/1985 Suss et al. .................. 523/216

FOREIGN PATENT DOCUMENTS

| 251553 | 7/1988 | European Pat. Off. |
| 1201064 | 9/1965 | Germany . |
| 3439128 | 5/1985 | Germany . |
| 941305 | 11/1963 | United Kingdom . |

OTHER PUBLICATIONS

European Polymer Journal, vol. 23, No. 2, 1987, Oxford, pp. 173–175, J.V. Dawkins, 'Non–Aqueous Poly (Methyl Methacrylate Dispersions: Radical Dispersion Polymerization in the Presence of the Diblock Copolymer Poly(Styrene–B–Methyl Methacrylate)'.

Antonietti et al, Makromol. Chem., Makromol. Symp., 30, 81–93 (1989).

Everett and Stageman, Discus. Faraday Soc., 65, 230 (1978).

Bamford et al, J. Appl. Polym. Sci, 25, 2559–2566 (1980).

*Primary Examiner*—Edward J. Webman
*Attorney, Agent, or Firm*—Bierman, Muserlian and Lucas

[57] ABSTRACT

The invention relates to a process for the preparation of a stable microdispersion of particles comprised of acrylic polymers in an organic solvent used as reaction medium in the presence of a stabilizing agent comprised of a block copolymer, characterized in that said acrylic polymer is obtained by radical polymerization of at least one acrylic monomer in the presence of a block copolymer based on polymethyl methacrylate (PMMA) and polytert-butyl acrylate (PtBuA).

It also relates to microdispersions which may be obtained by said process as well as to microgels produced from said microdispersions and compositions, particularly cosmetic compositions such as nail varnish.

24 Claims, No Drawings

STABLE MICRODISPERSIONS AND MICROGELS BASED ON ACRYLIC POLYMERS, METHOD FOR OBTAINING THEM AND COMPOSITIONS, PARTICULARLY COSMETIC COMPOSITIONS, CONTAINING THEM

The present invention relates to novel stable microdispersions of polymer particles, to the microgels obtained from these dispersions and to compositions, particularly cosmetic compositions, containing these microdispersions or microgels. It further relates to a method of preparing these dispersions and microgels.

In terms of the invention, microdispersion is understood as meaning a dispersion of particles whose size can range up to 120 nm and is preferably less than 100 nm. The polymer constituting these particles is in precipitated form in the reaction medium, the particles being stabilized by a copolymer.

In line with Antonietti et al. in "Makromol. Chem., Makromol. Symp." 30, 81–93 (1989), a microgel is defined according to the invention as being a micro-particle of crosslinked polymer, in swollen form, dispersed in an organic solvent; its size, which is governed by the swelling ratio, depends on the crosslinking density. The polymer of which the microgel is composed, in the non-crosslinked form, is soluble in this same solvent; only crosslinking prevents the particles from being dissolved.

The essential difference between a microdispersion and a microgel is the fact that the former exists in precipitated form in the reaction medium formed by a solvent which does not solubilize the polymer, whereas the microgel is in swollen form in solvents for the polymer.

By way of example, a PMMA microdispersion prepared in an alcoholic reaction medium exists in precipitated form because the alcohol is not a solvent for PMMA, the microdispersion in precipitated form being stabilized by the block copolymer. Being crosslinked, these same particles make it possible to obtain microgels in swollen form when they are transferred into a solvent for PMMA, such as butyl acetate.

Methods of preparing acrylic microgels in aliphatic hydrocarbons, either on their own or mixed with other hydrocarbons or with alcohols, have been described in a number of publications.

Thus patent U.S. Pat. No. 4 558 075 describes the preparation of acrylic microparticles in the presence of PGMA-PMMA-PMAA random copolymers in a reaction medium consisting of heptane, and their application in the field of automotive paint containing aluminum flakes. The polymer particles have dimensions of between 0.01 and 10μ.

D. H. EVERETT and J. F. STAGEMAN (Discus. Faraday Soc. 65, 230, 1978) have described the preparation of polystyrene or PMMA dispersions in the presence of PDMS-b-PS-b-PDMS three-block copolymers using alkanes as the reaction medium. The polymer particles obtained according to said document have dimensions of the order of 0.1μ.

J. V. DAWKINS, S. A. SHAKIR and T. G. CROUCHER, Europ. Polym. J. 23, 173–175, 1987, have described the synthesis of PMMA dispersions in cyclohexane in the presence of PS-PMMA copolymers as stabilizers.

German patent DE 3 439 128 describes the preparation of acrylic microgels, stabilized either by polyesters or by copolymers of the "polyhydroxystearic acid-PMMA-PAA" type, in a reaction medium consisting of water or aliphatic hydrocarbons, and their applications in the preparation of metallic lacquers based on aqueous microgels or white lacquers based on titanium oxide in the case of microgels in aliphatic hydrocarbons. The dimensions of the polymer particles described in said document are of the order of 0.01 to 10μ.

Other publications cite the use of mixtures of hydrocarbons and alcohols as the reaction medium. This is the case of European patent EP 251 553, in which acrylic microgels are prepared in the presence of copolymerizable stabilizers, which are copolymerized with acrylic monomers to produce a core-shell. The dispersions obtained can be used for painting metals.

This is also the case of the publication by C. H. BAMFORD et al., J. Appl. Polym. Sci., 25, 2559–2566, 1980, which again describes microgels in a solvent medium consisting of a mixture of alcohol and hydrocarbon, except that the use of a surface-active stabilizer is dispensed with.

It therefore appears that, as far as acrylic microgels are concerned, the stabilizing copolymers are generally graft or random copolymers based on polymethyl methacrylate. The publication by J. V. DAWKINS et al., Euro. Polym. J. 23, 173–175, 1987, uses PMMA-b-PS block copolymers as stabilizers for polymethyl methacrylate dispersions.

British patent GB 941 305 describes the preparation of acrylic polymers, stabilized by block copolymers which are also acrylic, in ethyl alcohol. The stabilizing part of the copolymer employed in said patent is composed of polymethacrylic acid. The sizes of the particles constituting the dispersions described in patent GB 941 305 are of the order of 0.2μ or more. Furthermore, the dispersions obtained by following the teaching of said patent have dry extracts of between 25 and 65%.

In the course of its researches, the Applicant has discovered that, by using as the stabilizer a block copolymer based on polymethyl methacrylate (PMMA) and polytert-butyl acrylate (PtBuA), it is possible to prepare, in an alcoholic medium, microdispersions of acrylic polymer particles whose dimensions are much smaller than those described hitherto, being less than 120 nm and generally of the order of 80 nm, which is of great advantage in terms of the stability of said dispersion.

These particles also have a low size polydispersity index characterized by the ratio Dw/Dn, where Dw is the weight-average size and Dn the number-average size.

By virtue of their small size, these particles have a large specific surface area, which can be a favorable factor in compositions containing pigments or fillers.

Furthermore, the microdispersions of the invention also have the advantage of being able to be concentrated, or even dried, and redispersed in a solvent, for example an alcohol, while retaining the same characteristics.

Another advantage of the microdispersions according to the invention is that they are compatible with esters to form microgels.

The advantages and characteristics of the invention are apparent from the following description.

According to one of these essential characteristics, the invention relates to a method of preparing a stable microdispersion of particles consisting of acrylic polymers, in an organic solvent used as the reaction medium, in the presence of a stabilizer consisting of a block copolymer, characterized in that said acrylic polymer is obtained by the free-radical polymerization of at least one acrylic monomer in the presence of a block copolymer based on polymethyl methacrylate (PMMA) and polytert-butyl acrylate (PtBuA).

Thus the method of the invention consists in preparing an acrylic polymer by a known method of free-radical polymerization in a solvent, and in carrying out this polymerization in the presence of a block copolymer made up of PMMA and PtBuA.

This block copolymer advantageously has a molecular weight of between 20,000 and 500,000, preferably of between 40,000 and 200,000.

It can be either a two-block copolymer symbolically represented by PMMA-b-PtBuA, or a copolymer of the three-block type symbolized by PtBuA-b-PMMA-b-PtBuA.

In the case of the double block, the percentage by weight of the polytert-butyl acrylate block will be between 10 and 90% but preferably close to 50%.

In one advantageous variant of the method, the acrylic monomer is selected from the family of alkyl acrylates and alkyl methacrylates having linear or branched $C_1$ to $C_{18}$ alkyl groups, or mixtures thereof. Methyl, butyl and lauryl groups may be mentioned as examples of alkyl groups. Methyl methacrylate, butyl acrylate or a mixture of these two monomers may be mentioned as preferred examples of acrylic monomers. Mixtures of methyl methacrylate and lauryl methacrylate may also be mentioned.

These acrylic monomers will advantageously be copolymerized, according to the method of the invention, with a difunctional monomer.

Divinylbenzene and diacrylic or dimethacrylic monomers, for example butanediol dimethacrylate, ethylene glycol dimethacrylate, diethylene glycol dimethacrylate and tetraethylene glycol dimethacrylate, may be mentioned as examples of difunctional monomers.

A preferred difunctional monomer according to the invention is butanediol dimethacrylate (BDMA).

The amount of block copolymer used to form the microdispersions of the present invention is advantageously between 1 and 50% by weight, preferably between 5 and 30%, and more preferably of the order of 10% based on all the monomers used to prepare said acrylic polymer.

The reaction medium used is an alcohol, in particular a $C_1$ $C_4$ alcohol, preferably ethanol, or a mixture of alcohols defined above, for example a mixture of ethanol and isopropanol.

The reaction medium used can also be any solvent which solubilizes the PtBuA chain of the stabilizing copolymer and which precipitates the PMMA chain of this same copolymer and the acrylic polymer formed. An alcohol-rich medium can be used in particular, examples being a mixture of ethanol with 20% by volume of butyl acetate or a mixture of ethanol with 20% by volume of ethyl acetate.

The free-radical polymerization is carried out in conventional manner in the presence of a free-radical polymerization initiator consisting of an organosoluble initiator preferably selected from the family of azo initiators and peroxides.

Azobisisobutyronitrile and benzoyl peroxide may be mentioned as examples of preferred initiators.

Advantageously the free-radical polymerization is carried out in several steps comprising the preparation of a seed followed by the gradual addition of the remaining products.

The seed will preferably consist of about 20% of the mixture of monomers and crosslinking agent and about 50% of the initiator. This mixture will be added to the preformed micellar solution of the copolymer in alcohol at the polymerization temperature; the polymerization is preferably carried out at about 5° to 10° C. below the boiling point of the solvent constituting the reaction medium, and is allowed to proceed for about 4 h.

The remaining constituents, but preferably all the initiator remaining dissolved in alcohol, and the monomers will be added slowly to the resulting seed over a period advantageously of between 2 and 4 h.

The synthesis will be stopped after an additional polymerization time of the order of 16 h.

The above-described microdispersions of acrylic polymers have particle dimensions and a monodispersity which have never been attained hitherto for dispersions in an alcoholic medium. They constitute industrial products which are novel per se.

Thus, according to another of its aspects, the invention relates to the acrylic polymer dispersions which can be obtained by the method described above.

The dispersions are composed of particles having dimensions of less than 120 nm, generally of the order of 80 nm, and a low polydispersity index (between 1.1 and 1.2).

Furthermore, these microdispersions have the following advantages:

the microdispersions are compatible with esters, such as butyl acetate, to form microgels;

the products obtained are compatible with nitrocellulose dissolved in butyl acetate to give a transparent and glossy film;

the polymer obtained does not contain acid groups, these generally being detrimental to nitro-cellulose-based formulations;

crosslinking of the particles enables the rheological characteristics to be adjusted; and the microdispersions prepared in this way can be used to obtain nail varnishes in an alcoholic medium.

Thus, according to another of its aspects, the invention relates to the microgels obtained from the microdispersions of the invention. More precisely, these microgels are obtained by transferring the particles into a solvent for PMMA, either after prior drying of the microdispersions or by adding this same solvent to the microdispersion concentrated beforehand.

Solvents which may be mentioned are aromatic solvents, chlorinated solvents such as chloroform or methylene chloride, ketones and esters such as $C_2$ to $C_4$ alkyl acetates, more particularly butyl acetate and ethyl acetate.

Principally to avoid obtaining excessively viscous microgels, and hence to facilitate their use, the concentration by weight of polymers in the microgels, in particular when the latter are intended for the formulation of varnishes such as nail varnishes, does not generally exceed about 30%. This proportion is preferably between about 10% and 20%.

The dispersions and microgels of the invention prove particularly useful in the fields of paint and cosmetics, where they enable the rheological characteristics to be adjusted. In fact, the microdispersion can be mixed with nitrocellulose-based formulations of high dry extract without appreciably increasing the viscosity of the resulting system.

The fact that the products are compatible with nitrocellulose dissolved in butyl acetate to give a transparent and glossy film makes it possible to contemplate their use for the preparation of varnishes, particularly nail varnishes.

More precisely, the use of the microgels of the invention in varnish formulations, especially nail varnish formulations, has the following advantages in particular:

it enables the rheological properties to be improved, making it possible in particular to avoid precipitation of the pigments, and enables the reproducibility of these properties to be improved. In particular, this makes it possible substantially to reduce the amount of, or even dispense with, the bentone which is generally used for this purpose despite its well-known disadvantages;

it enables the dry extract of the film formed by the varnish to be increased without thereby substantially increasing the viscosity of the varnish;

it gives the film more gloss; and it reinforces the thixotropic effect provided by bentone in an acetate medium.

The proportion by weight of microgel according to the invention in the final composition of the varnish can range up to about 30%, for example in the case where it is desired to reduce the amount of nitrocellulose or dispense with it. In general, however, it is preferred to use proportions of between about 5 and 20% by weight.

The Examples which follow are given purely in order to illustrate the invention.

EXAMPLES

Example 1

Preparation of a Microdispersion According to the Invention

The two-block copolymer used in this Example (copolymer I) has a number-average molecular weight of 90,000 and comprises 50% by weight of PtBuA; the PtBuA and PMMA blocks have Mn values of 45,000 each.

In a jacketed reactor equipped with a condenser and a nitrogen inlet, 150 g of ethanol and 0.76 g of copolymer are heated at 65° C. for 30 minutes, with stirring.

0.2 g of azobisisobutyronitrile (AIBN), 1.5 g of methyl methacrylate (MMA) and 0.075 g of butanediol dimethacrylate (BDMA) are then added and polymerization is allowed to proceed for 4 h.

0.2 g of AIBN dissolved in 20 ml of ethanol is introduced, this being followed by the addition of 5.70 g of MMA and 0.29 g of BDMA at a rate of 2.5 ml/h. When the addition is complete, the polymerization is continued for about 16 h. The microdispersion obtained has a dry extract of 4.1%, the particles have a size of 98 nm and the value of Dw/Dn is 1.12.

Example 2

Preparation of a Microdispersion

The method of synthesis is the same as that given for Example 1, the only change being the proportions of the various constituents.

Preparation of the seed:

| 150 g   | EtOH        |
|---------|-------------|
| 1.87 g  | copolymer I |
| 0.2 g   | AIBN        |
| 0.53 g  | BuA         |
| 0.97 g  | MMA         |
| 0.075 g | BDMA        | followed by the addition of 0.2 g of AIBN in 20 ml of EtOH and then by the addition of:

| 2.0 g  | BuA  |
|--------|------|
| 3.7 g  | MMA  |
| 0.29 g | BDMA | at 2.5 ml/h.

The dispersion obtained has a dry extract of 4.7%, the particles obtained have a size of 86.5 nm and the value of Dw/Dn is 1.14.

Example 3

Demonstrating the Possibility of Using a Copolymer of Higher Molecular Weight The two-block copolymer employed in this Example (copolymer II) has a number-average molecular weight of 150,000 and comprises 75% by weight of PtBuA; the PtBuA and PMMA blocks have Mn values of 112,500 and 37,500 respectively.

The procedure is unmodified, the proportions of the various constituents being as follows:

Preparation of the seed:

| 150 g   | EtOH         |
|---------|--------------|
| 1.87 g  | copolymer II |
| 0.2 g   | AIBN         |
| 0.75 g  | MMA          |
| 0.75 g  | BuA          |
| 0.075 g | BDMA         | followed by the addition of 0.2 g of AIBN in 20 ml of EtOH and then by the addition of:

| 2.85 g | MMA  |
|--------|------|
| 2.85 g | BuA  |
| 0.29 g | BDMA | at 2.5 ml/h.

The dispersion obtained has a final dry extract of 4.7%, a particle size of 94.3 nm and a Dw/Dn value of 1.15.

Example 4

Demonstrating the Possibility of Using a PMMA-Rich Copolymer

The two-block copolymer used here (copolymer III) has a number-average molecular weight of 80,000 and comprises 35.4% by weight of PtBuA; the PtBuA and PMMA blocks have Mn values of 28,300 and 51,700 respectively.

The course of the synthesis remains unchanged, the ingredients introduced being as follows:

Preparation of the seed:

| 150 g   | EtOH          |
|---------|---------------|
| 0.76 g  | copolymer III |
| 0.2 g   | AIBN          |
| 0.75 g  | BuA           |
| 0.75 g  | MMA           |
| 0.075 g | BDMA          | followed by the addition of 0.2 g of AIBN in 20 ml of EtOH and then by the addition of:

| 2.85 g | MMA  |
|--------|------|
| 2.85 g | BuA  |
| 0.29 g | BDMA | at 2.5 ml/h.

The dispersion obtained has a solids content of 4.3%, a particle size of 81.3 nm and a Dw/Dn of 1.14.

Example 5

Demonstrating the Influence of the Average Molecular Weight of the Block Copolymer The two-block copolymer IV used for this Example has a total Mn of 26,000, the percentage by weight of the PtBuA block being 85%.

The method of synthesis is the same, the proportions involved being as follows:

Preparation of the seed:

| | |
|---|---|
| 250 g | EtOH |
| 3 g | copolymer IV |
| 1.40 g | MMA |
| 0.07 g | BDMA |
| 0.1 g | AIBN | followed by the addition of 0.4 g of AIBN in 20 ml of EtOH and then by the addition of:

| | |
|---|---|
| 13.34 g | MMA |
| 0.29 g | BDMA | at 2.5 ml/h.

However, the dispersion has a substantially lower stability than the dispersions obtained with the polymers of $Mn \geq 40,000$.

Example 6

Preparation of a Microdispersion from an Acrylic Monomer Mixture

The two-block copolymer used in this Example has a number-average molecular weight of 53,000 and comprises 85% by weight of PtBuA and 15% of PMMA.

In a jacketed reactor equipped with a condenser and a nitrogen inlet, 150 g of an isopropanol/ethanol mixture containing 80% of isopropanol and 20% of ethanol, and 0.76 g of two-block copolymer, are heated at 65° C. for 30 minutes, with stirring.

0.2 g of AIBN, 1.62 g of MMA, 0.18 g of lauryl methacrylate (LMA) and 0.075 g of BDMA are then added. The polymerization is allowed to proceed for 4 h.

0.2 g of AIBN dissolved in 20 ml of an 80/20 isopropanol/ethanol mixture is introduced and 6.48 g of MMA, 0.72 g of LMA and 0.29 g of BDMA are added at a rate of 2.5 ml/h. When the addition is complete, the polymerization is continued for about 16 h. The microdispersion obtained has a dry extract of about 5.5% and the constituent particles have a size of about 108 nm.

Example 7

Demonstrating the Possibility of Using a Three-Block Copolymer of the PtBuA-b-PMMA-b-PtBuA Type

The three-block copolymer, copolymer V, has a number-average molecular weight of 30,000 and a percentage of PtBuA of 54% and the PMMA has an Mn of 14,000.

The course of the synthesis is the same as previously, the amounts introduced being as follows:

Preparation of the seed:

| | |
|---|---|
| 150 g | EtOH |
| 0.75 g | BuA |
| 0.075 g | BDMA | followed by the addition of 0.2 g of AIBN in 20 ml of EtOH and then by the addition of:

| | |
|---|---|
| 2.85 g | MMA |
| 2.85 g | BuA |
| 0.29 g | BDMA | at 2.5 ml/h.

The dispersion obtained has a dry extract of 4%, a particle size of 101 nm and a Dw/Dn of 1.13.

Example 8

Preparation of the Microgels and Compatibility with Nitrocellulose

There are several possible modes of preparing microgels. The simplest consists in drying the microdispersion completely on a rotary evaporator and redispersing the polymer in the appropriate amount of solvent for PMMA, for example butyl acetate, to give the microgel at the desired concentration.

Another method of obtaining the microgels consists in concentrating the microdispersion on a rotary evaporator and directly adding the amount of solvent for PMMA, for example butyl acetate, which is necessary to solubilize the PMMA. It is generally considered that the amount of solvent for PMMA has to represent a volume of more than 20% of the total volume of solvent.

In this same method, a solution of nitrocellulose dissolved in butyl acetate can also be added directly to the concentrated microdispersion.

By way of example, the latter method can be illustrated as follows:

The microdispersion obtained in Example 3 is concentrated on a rotary evaporator at 40° C. until a microdispersion with a concentration of 20% in ethanol is obtained. This has a viscosity of $7.0.10^{-3}$ Pa.s (7 cP) at 20° C., compared with $1.2.10^{-3}$ Pa.s (1.2 cP) for ethanol alone at the same temperature.

A mixture of equal proportions of the same 20% microdispersion in ethanol and a 20% solution of nitrocellulose of the type CA4 A20 in butyl acetate, with a viscosity of $17.9.10^{-3}$ Pa.s (17.9 cP), has a viscosity of $31.6.10^{-3}$ Pa.s (31.6 cP).

The solutions obtained are limpid and do not exhibit any phase separation, even on storage, demonstrating the compatibility between the microgels and nitrocellulose.

Example 9

Preparation of Nail Varnishes

Different nail varnishes are prepared by introducing into a nitrocellulose base a microgel according to the invention obtained from the microdispersion of Example 1 by dispersing the polymer in butyl acetate using a stirrer of the deflocculating type. The proportion of microgel is about 5 to 20%, based on the total weight of the varnish prepared in this way.

By way of example, the nitrocellulose bases used to prepare the nail varnishes have the following compositions in percentages by weight:

| | |
|---|---|
| nitrocellulose | 10 to 20 |
| arylsulfonamide resin (Santolite ® or | 10 to 15 |

-continued

| | |
|---|---|
| Lustralite ®) polyester resin | 2 to 5 |
| solvents (butyl acetate/ethyl acetate/ toluene mixture comprising less than 40% of toluene) | 60 to 80 |
| plasticizer: | 0.5 to 8 |
| dibutyl phthalate Citroflex-A2 ® camphor | |
| suspending agent, for example bentone | 0 to 1.5 |
| pigments | 0 to 2 |

Example 10

Nail Varnish

A nail varnish formulation comprising the following proportions in percentages by weight is prepared according to Example 9:

| | |
|---|---|
| nitrocellulose | 15 |
| microgel according to the invention | 15 |
| dibutyl phthalate | 1 |
| solvent (composed of 55% of ethyl acetate, 15% of butyl acetate and 30% of toluene) | 68 |
| pigments | 1 |

What is claimed is:

1. In a method of preparing a stable microdispersion of particles of acrylic polymers in an organic solvent in the presence of a stabilizer the improvement comprising: forming said acrylic polymer by a free-radical polymerization of at least one acrylic monomer in the presence of a block copolymer as said stabilizer, wherein said block copolymer is a copolymer of polymethyl methacrylate (PMMA) and polytert-butyl acrylate (PtBuA) and said solvent solubilizes said PtBuA chain of said copolymer and precipitates both said PMMA chain of said copolymer and said acrylic polymer.

2. The method according to claim 1 wherein said block copolymer has a molecular weight between 20,000 and 500,000.

3. The method according to claim 1 wherein the block copolymer is a two-block copolymer and PtBuA represents 10 to 90% by weight of said block copolymer.

4. The method according to claim 1 wherein said block copolymer is a three-block copolymer of PtBuA-b-PMMA-b-PtBuA.

5. The method according to claim 1 wherein said acrylic monomer is an alkyl acrylate or an alkyl methacrylate, said alkyls being linear or branched $C_1$ to $C_{18}$ alkyls, or a mixture of said monomers.

6. The method according to claim 1 wherein the acrylic polymer is a copolymer of at least one acrylic monomer and a difunctional monomer.

7. The method according to claim 6 wherein the difunctional monomer is butanediol dimethacrylate (BDMA).

8. The method according to claim 1 wherein the block copolymer is present in an amount between 1 and 50% by weight based on the monomer.

9. The method according to claim 1 wherein the solvent is an alcohol, a mixture of alcohols, or an alcohol-rich medium.

10. The method according to claim 9 wherein said solvent is ethanol.

11. The method according to claim 1 wherein said free-radical polymerization is carried out in the presence of an initiator belonging to the family of azo compounds and peroxides.

12. The method according to claim 11 wherein said initiator is azobisisobutyronitrile or benzoyl peroxide.

13. The method according to claim 1 wherein said polymerization comprises sequential steps of preparing a seed followed by gradually adding the remaining reactants.

14. A microdispersion of acrylic particles obtained by the method according to claim 1.

15. A method for making a microgel comprising the steps of: drying or concentrating a microdispersion obtained by the method of claim 1; and then combining the dried or concentrated microdispersion with a solvent for PMMA to form a microgel.

16. A microgel made by a process comprising the steps of:

(a) forming a stable microdispersion of particles of acrylic polymers in an organic solvent wherein said acrylic polymer is formed by a free-radical polymerization of at least one acrylic monomer in the presence of a block copolymer, said block copolymer being a copolymer of polymethyl methacrylate (PMMA) and polytert-butyl acrylate (PtBuA);

(b) drying or concentrating said stable microdispersion of particles, and then transferring said dried or concentrated stable microdispersion of particles to a solvent for PMMA to form a microgel; and (c) recovering said microgel.

17. The microgels according to claim 16 wherein said solvent for PMMA is selected from the group comprising aromatic solvents, chlorinated solvents such as chloroform or methylene chloride, ketones and esters such as a $C_2$ to $C_4$ alkyl acetate.

18. The microgels according to claim 16 wherein said solvent for PMMA is butyl acetate or ethyl acetate.

19. The microgels according to claim 16 wherein the concentration by weight of polymer in the solvent for PMMA is less than 30%.

20. A cosmetic composition comprising a microdispersion of acrylic particles obtained by the method according to claim 1.

21. A cosmetic composition comprising a microgel according to claim 16.

22. The composition according to claim 21 wherein it contains less than 30% by weight of said microgel.

23. A nail polish composition comprising a microdispersion of acrylic particles obtained by the method according to claim 1.

24. A nail polish composition comprising a microgel according to claim 16.

* * * * *